United States Patent
Nichols et al.

(10) Patent No.: US 9,980,831 B2
(45) Date of Patent: May 29, 2018

(54) URETERAL STENT

(71) Applicant: FutureMatrix Interventional, Athens, TX (US)

(72) Inventors: David L. Nichols, Brownsboro, TX (US); Christopher A. Richardson, Athens, TX (US)

(73) Assignee: FUTUREMATRIX INTERVENTIONAL, Athens, TX (US)

( * ) Notice: Subject to any disclaimer, the term of this patent is extended or adjusted under 35 U.S.C. 154(b) by 0 days. days.

(21) Appl. No.: 15/011,281

(22) Filed: Jan. 29, 2016

(65) Prior Publication Data

US 2016/0220397 A1    Aug. 4, 2016

Related U.S. Application Data

(60) Provisional application No. 62/110,337, filed on Jan. 30, 2015.

(51) Int. Cl.
| | |
|---|---|
| *A61F 2/04* | (2013.01) |
| *A61F 2/848* | (2013.01) |
| *A61M 27/00* | (2006.01) |
| *A61F 2/00* | (2006.01) |
| *A61L 31/06* | (2006.01) |
| *A61M 25/00* | (2006.01) |
| *A61M 25/01* | (2006.01) |

(52) U.S. Cl.
CPC ............ *A61F 2/848* (2013.01); *A61F 2/0095* (2013.01); *A61F 2/04* (2013.01); *A61L 31/06* (2013.01); *A61M 27/008* (2013.01); *A61F 2002/048* (2013.01); *A61F 2210/00* (2013.01); *A61F 2240/001* (2013.01); *A61M 25/002* (2013.01); *A61M 25/0009* (2013.01); *A61M 25/0102* (2013.01); *A61M 2207/00* (2013.01)

(58) Field of Classification Search
CPC ...................................... A61F 2/04; A61F 2/06
USPC ............................. 623/23.65–23.7, 1.15–1.48
See application file for complete search history.

(56) References Cited

U.S. PATENT DOCUMENTS

| | | | |
|---|---|---|---|
| 6,743,198 | B1 | 6/2004 | Tihon |
| 2003/0040754 | A1 | 2/2003 | Mitchell et al. |
| 2004/0193283 | A1 | 9/2004 | Rioux et al. |
| 2007/0225679 | A1 | 9/2007 | Deal |

(Continued)

FOREIGN PATENT DOCUMENTS

| | | |
|---|---|---|
| WO | 2008/036711 | 3/2008 |
| WO | PCT/US2016/015809 | 4/2016 |

OTHER PUBLICATIONS

International Search Report dated Apr. 19, 2016 for PCT application No. PCT/US2016/015809.

(Continued)

*Primary Examiner* — Suzette J Gherbi
(74) *Attorney, Agent, or Firm* — Evan Law Group LLC

(57) ABSTRACT

A ureteral stent comprises an internal portion, which comprises a first polymer, and an external portion, which comprises a second polymer. The external portion surrounds the internal portion and has a plurality of radial projections that extend along the length of the ureteral stent. The second polymer has a Shore D hardness of 20-40 Shore D. The first polymer has a Shore D hardness that is at least 10 units greater than the Shore D hardness of the second polymer.

18 Claims, 8 Drawing Sheets

(56) References Cited

U.S. PATENT DOCUMENTS

| | | | |
|---|---|---|---|
| 2009/0171465 A1 | 7/2009 | Bucay-Couto et al. | |
| 2009/0248169 A1 | 10/2009 | Li | |
| 2010/0286791 A1 | 11/2010 | Goldsmith | |
| 2013/0325143 A1* | 12/2013 | Lamson | A61B 17/0401 623/23.66 |
| 2014/0081380 A1* | 3/2014 | Giasolli | A61F 2/82 623/1.15 |
| 2015/0051693 A1* | 2/2015 | Bertolino | B29C 45/372 623/1.13 |
| 2016/0038273 A1* | 2/2016 | Eisner | A61F 2/04 623/23.68 |
| 2016/0157987 A1* | 6/2016 | Tang | A61M 27/008 623/23.7 |
| 2016/0331383 A1* | 11/2016 | Hebert | A61B 17/12172 |
| 2016/0331853 A1* | 11/2016 | Taub | A61K 47/48853 |
| 2017/0056213 A1* | 3/2017 | Firstenberg | A61F 2/07 |
| 2017/0065398 A1* | 3/2017 | Bertolino | B29C 45/372 |
| 2017/0079818 A1* | 3/2017 | Pendleton | A61M 27/008 |

OTHER PUBLICATIONS

"Urinary system", Wikipedia, pp. 1-4, found at en.wikipedia.org/wiki/Urinary_system, printed on Jul. 2, 2015.

"Ureter", Wikipedia, pp. 1-4, found at en.wikipedia.org/wiki/Ureter, printed on Jun. 24, 2015.

"Ureteric stent", Wikipedia, pp. 1-3, found at en.wikipedia.org/wiki/Ureteric_stent, printed on Jul. 1, 2015.

"Towers Peripheral Ureteral Stent Set", Cook Medical, found at www.cookmedical.com/products/uro_towers_webds/ (2015).

Singh, I., "Indwelling JJ ureteral stents—a current perspective and review of literature", Indian Journal of Surgery, vol. 65, No. 5, pp. 405-412, (2003).

"PEBAX® Polyether Block Amides", Arkema, pp. 1-14, found at www.PEBAX.com/export/sites/PEBAX/.content/medias/downloads/literature/PEBAX-procuct-range-brochure.pdf, printed on Jul. 17, 2015.

* cited by examiner

URETERAL STENT

BACKGROUND

The urinary system (or renal system) includes the kidneys, the ureters, the bladder and the urethra. The kidneys filter and process blood, secreting soluble wastes in the form of urine. Urine travels from the individual kidneys through their respective ureters and into the bladder before being expelled from the body through the urethra.

Proper functioning of the urinary system may be impaired by damage to any of its components. The ureters are particularly vulnerable due to their small, thin shape. A ureter may be damaged during a medical procedure, such as a hysterectomy or an ureteroscopy, or as a result of trauma, such as a high-speed vehicular accident or a penetrating abdominal injury. Tumors, both in the ureter and in surrounding tissues, may exert pressure that compresses the ureter. A ureter may become obstructed due to kidney stones that become lodged in the ureter and restrict or block the flow of urine. As the only conduit for urine to leave the kidneys, it is extremely important to preserve the flow of urine through the ureter. A blocked ureter may lead to serious medical conditions, such as hydronephrosis in the corresponding kidney.

The patency of a ureter may be maintained by inserting a ureteral stent (also known as a ureteric stent) into the ureter. A ureteral stent is a thin tube that creates a passageway through the ureter and ensures that urine can travel from the kidneys to the bladder. In addition to maintaining the flow of urine through the ureter, ureteral stents are also used to promote healing of the ureter, to dilate the ureter prior to a medical procedure and to bypass obstructions within the ureter.

While early ureteral stents were simple tubes, modern ureteral stents incorporate a number of design features to prevent complications such as migration and occlusion. The portions of a ureteral stent that extend into the kidney and bladder may be curved or coiled to prevent the stent from becoming displaced. Ureteral stents with curved or coiled ends are referred to as JJ stents, double J stents or pigtail stents. The exterior of a ureteral stent may include channels that provide paths for urine flow in addition to the central lumen of the ureteral stent. The channels ensure that the ureteral stent remains functional if the central lumen becomes occluded or blocked.

These designs may reduce stent failure, but do not address the pain, discomfort or irritation (also referred to as colic) that many patients experience in the kidney, bladder or groin region. Stent pain and discomfort may occur spontaneously, while urinating, during strenuous physical activity or during sexual intercourse. Patients who experience pain or irritation often go to the emergency room due to the intensity and location of the symptoms. Treatment frequently involves removal of the ureteral stent. If the underlying issue that necessitated placing the ureteral stent has not resolved, the patient will require insertion of a new stent. Hospital visits and repeat stenting procedures can result in substantial medical expenses for patients and insurers.

An early solution to patient discomfort was forming ureteral stents entirely out of silicone. Silicone ureteral stents were well-tolerated by patients, but medical professionals found these stents difficult to handle and insert due to their lack of rigidity. As a result, silicone ureteral stents were phased out of the market.

SUMMARY

In a first aspect, the invention is a ureteral stent including an internal portion, which comprises a first polymer, and an external portion, which comprises a second polymer. The external portion surrounds the internal portion and has a plurality of radial projections that extend along the length of the ureteral stent. The second polymer has a Shore D hardness of 20-40 Shore D. The first polymer has a Shore D hardness that is at least 10 units greater than the Shore D hardness of the second polymer.

In a second aspect, the invention is a method of making a ureteral stent, comprising co-extruding a first polymer and a second polymer.

In a third aspect, the invention is a method of stenting a patient, comprising inserting a ureteral stent into a ureter.

In a fourth aspect, the invention is a kit, including a guidewire and a ureteral stent. The guidewire and the ureteral stent are sterile.

Definitions

The term "radial projection" means a member that extends away from the central axis of a ureteral stent.

The term "lobe" means a protrusion that extends from a radial projection.

The term "lumen" means a passage through the center of a ureteral stent. One end of the lumen opens into the kidney while the opposite end of the lumen opens into the bladder. A "closed lumen" is a lumen that is fully enclosed by the internal portion of a ureteral stent. An "open lumen" is a lumen that is not fully enclosed by the internal portion of a ureteral stent. For example, an open lumen may be formed by a ureteral stent that is C-shaped in cross section.

The term "co-extrusion" means a polymer manufacturing process in which multiple polymers are simultaneously extruded to form a single product.

The term "stenting" means the process of placing a stent in a patient.

The term "guidewire" means a thin, flexible wire used for placing a ureteral stent.

The term "pusher" means a thin, flexible tube that fits over a guidewire and is used for advancing a ureteral stent along the guidewire.

BRIEF DESCRIPTION OF THE DRAWINGS

The invention can be better understood with reference to the following drawings and description.

DETAILED DESCRIPTION

The present invention is a ureteral stent that is significantly more comfortable than existing stents. The ureteral stent has a plurality of radial projections and is composed of at least two polymers, each having a different hardness. The exterior of the ureteral stent is composed of the softer polymer to provide a device that is less irritating to patients, while the interior of the ureteral stent is composed of the harder polymer to provide the rigidity needed for handling and insertion. Patient comfort is also improved by radial projections that minimize contact between the ureteral stent and the ureter. These design features improve the patient experience and produce significant cost savings by reducing the need for medical intervention after the stent has been placed.

In addition to increasing patient comfort, the ureteral stent also provides clinical advantages during stent placement. As compared to the softer polymer, the harder polymer has a lower coefficient of friction with the guidewire used during stent insertion. The reduced coefficient of friction results in improved guidewire tracking and more accurate manipulation of the ureteral stent.

Figure 1:
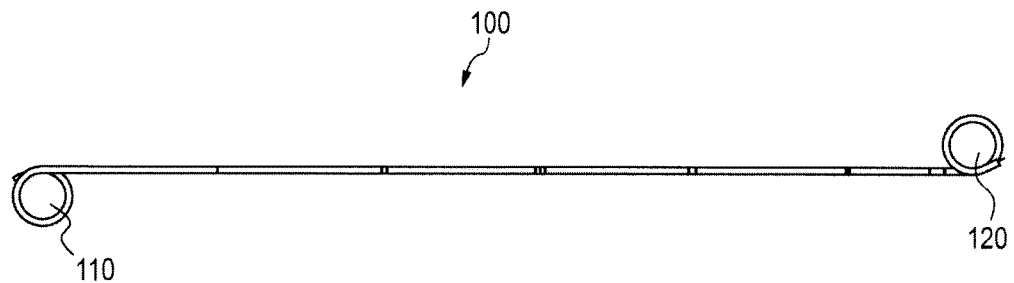
FIG. 1 illustrates a top view of a ureteral stent.

FIG. 1 illustrates a top view of a ureteral stent 100. When the ureteral stent has been properly placed in a ureter, the kidney end 110 rests in the patient's kidney and the bladder end 120 rests in the patient's bladder. The kidney end and/or the bladder end may optionally be coiled, as illustrated, to reduce the possibility of dislocation. The kidney end and the bladder end may be identical, and may be interchangeable.

Figure 2:
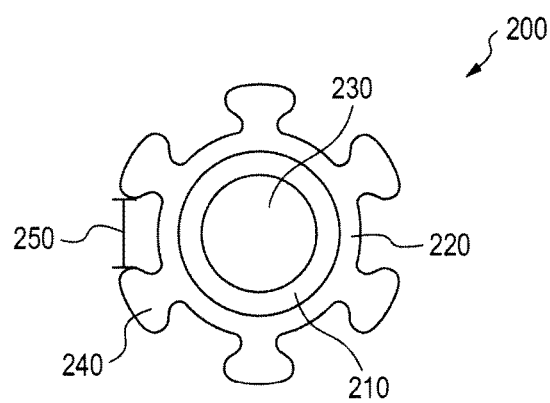
FIG. 2 illustrates a cross section of a ureteral stent having an optional closed lumen.

FIG. 2 illustrates a cross section of a ureteral stent 200 having an optional closed lumen 230. The ureteral stent includes an internal portion 210 composed of a first polymer and an external portion 220 composed of a second polymer. The optional closed lumen runs through the center of the ureteral stent. The external portion includes a plurality radial projections 240 (for example, six as illustrated) that define external channels 250. Preferably, the ureteral stent is sterile.

Figure 3:
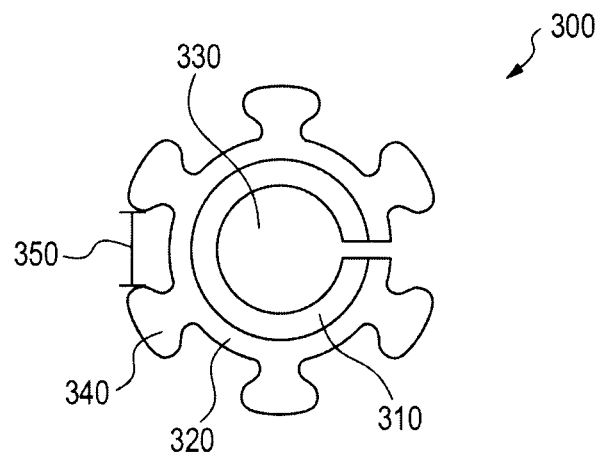
FIG. 3 illustrates a cross section of a ureteral stent having an optional open lumen.

FIG. 3 illustrates a cross section of a ureteral stent 300 having an optional open lumen 330. The ureteral stent includes an internal portion 310 composed of a first polymer and an external portion 320 composed of a second polymer. The optional open lumen runs through the center of the ureteral stent. The external portion includes a plurality radial projections 340 (for example, six as illustrated) that define external channels 350.

The first polymer and the second polymer each have a different hardness. The first polymer provides the rigidity necessary for handling and insertion, while the second polymer is selected to improve patient comfort since it is the only portion of the ureteral stent that is in direct contact with the ureter. The hardness of the polymers may be determined using a durometer and may be measured in units of Shore D. The first polymer has a Shore D hardness that is at least 10 units greater than the Shore D hardness of the second polymer. Preferably, the first polymer has a hardness of 35-70 Shore D, including 35, 40, 45, 46, 47, 48, 49, 50, 51, 52, 53, 54, 55, 56, 57, 58, 59, 60, 61, 62, 63, 64, 65 and 70 Shore D. Preferably, the second polymer has a hardness of 20-40 Shore D, including 20, 21, 22, 23, 24, 25, 26, 27, 28, 29, 30, 31, 32, 33, 34, 35 and 40 Shore D. The polymers may be thermoplastic elastomers. Preferred thermoplastic elastomers include polyurethanes and polyether block amides, such as PEBAX® (Arkema, France).

Figure 11:
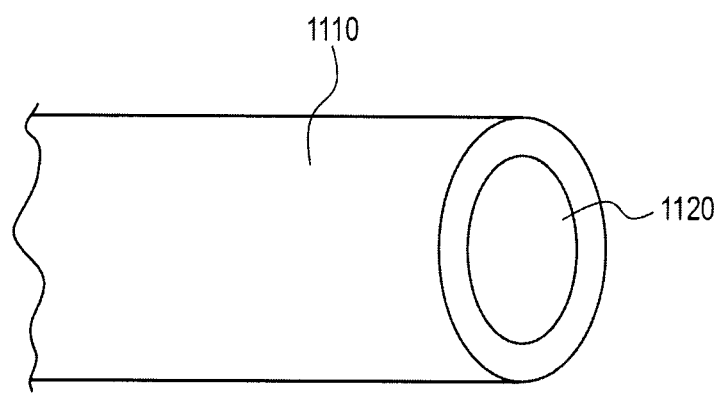
FIG. 11 illustrates a partial view of the terminal portion of a ureteral stent.

The optional lumen is the internal portion defined by the material of the ureteral stent. FIG. 11 illustrates a partial view of the terminal portion of a ureteral stent 1110 (the radial projections have not been illustrated for clarity). The lumen has a portal 1120 for urine to enter and exit the ureteral stent. The lumen of the ureteral stent provides the primary pathway for urine to flow from the kidney to the bladder. One end of the lumen has a portal that opens into the kidney and the other end has a portal that opens into the bladder.

Figure 4:
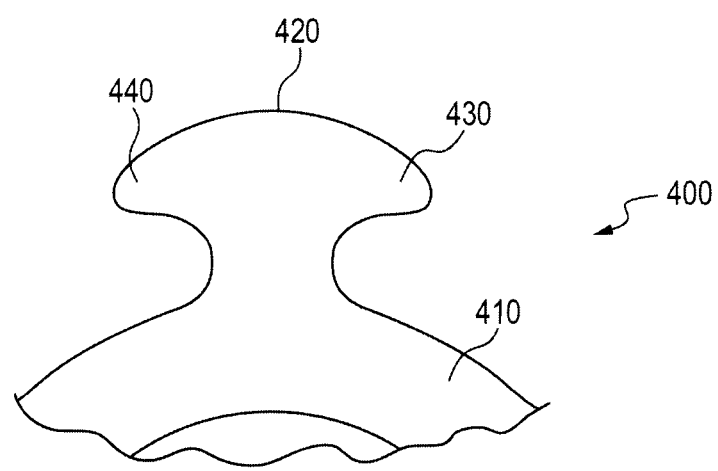
FIG. 4 illustrates a radial projection.

FIG. 4 illustrates a radial projection 400. The radial projection extends from the external portion 410 of a ureteral stent (partially shown). The terminal portion 420 of the radial projection is curved to approximate the curvature of the inner surface of a ureter. The radial projection includes an optional first lobe 430 and an optional second lobe 440 extending in opposite directions from the terminal portion of the radial projection.

The radial projections may extend from the external portion of the ureteral stent, or may form the external portion of the ureteral stent. Preferably, the ureteral stent includes 2, 3, 4, 5, 6, 7, 8, 9 or 10 radial projections. When the ureteral stent has been placed in a ureter, the radial projections exert a slight outward pressure on the inner surface of the ureter. This pressure helps keep the ureteral stent in place and reduces the need to coil the ends of the ureteral stent.

Figure 5:
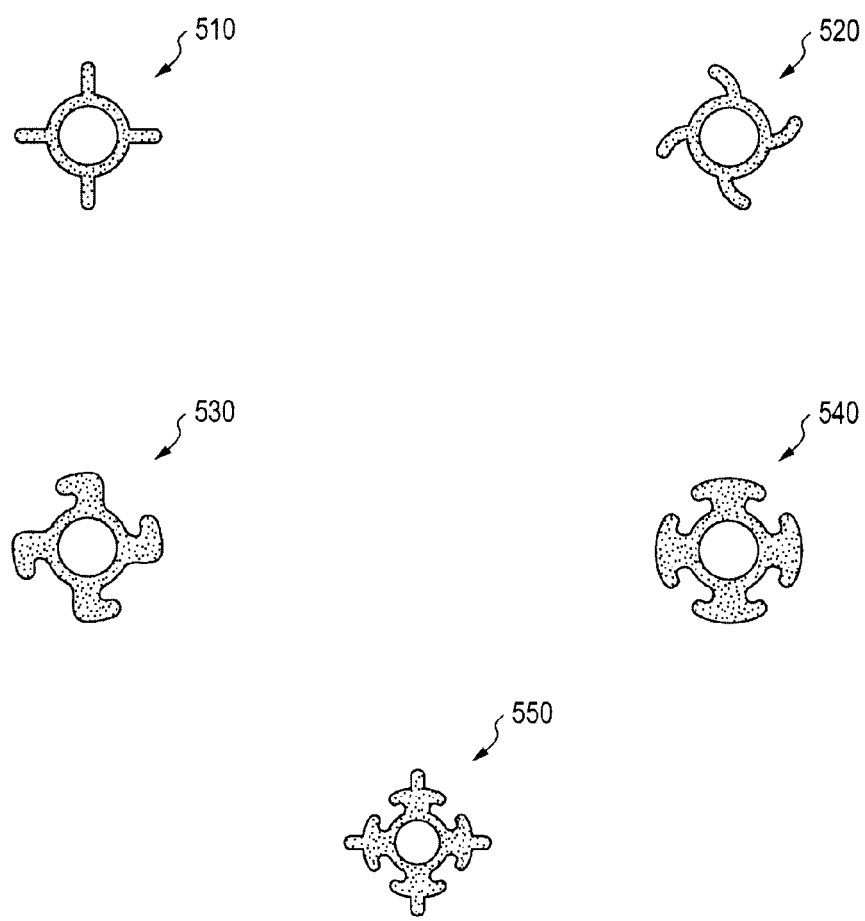
FIG. 5 illustrates cross sections of ureteral stents having different shapes of radial projections.

The radial projections may have a variety of shapes and configurations. FIG. 5 illustrates cross sections of alternative configurations of ureteral stents having different shapes of radial projections. The radial projections may be straight and extend substantially normal to the external portion of a ureteral stent as shown at 510. The radial projections may alternatively be curved as shown at 520. The radial projections may optionally include one or more lobes. The lobes may extend in either direction at any angle from any point along the radial projections. A ureteral stent with radial projections having a single lobe each is shown at 530. Preferably, the single lobes are located at the terminal ends of the radial projections and extend in the same direction. A ureteral stent with radial projections having two lobes each is shown at 540. The two lobes may extend in two different directions, or may extend in the same direction. Preferably, the two lobes are located at the terminal ends of the radial projections and extend in opposite directions. A ureteral stent with radial projections having three lobes may be formed by two lobes located between the external portion of the ureteral stent and the terminal portion of the radial projection as shown at 550. Preferably, a three-lobed radial projection has lobes which are equally spaced around the radial projection.

The radial projections define an equivalent number of external channels, as shown in FIG. 2 and FIG. 5. The external channels provide multiple paths for urine flow in addition to the lumen. The number of radial projections is inversely proportional to the size of the channels such that increasing the number of projections decreases the size of the channels. Preferably, the radial projections are evenly spaced around the ureteral stent to provide channels of equal size. However, the radial projections may be unevenly spaced around the ureteral stent to provide channels with unequal sizes, which may be desirable to accommodate kidney stones or other obstructions within the ureter.

Figure 6:
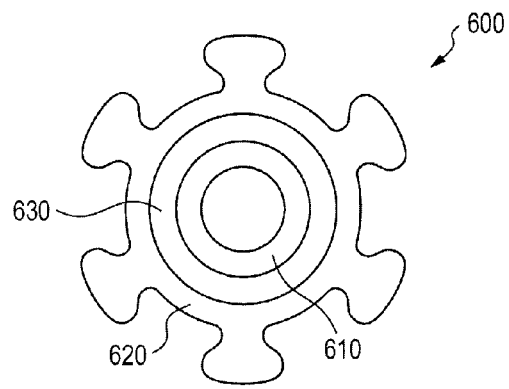
FIG. 6 illustrates a cross section of a ureteral stent composed of three polymers.

The ureteral stent may be composed of more than two polymers. FIG. 6 illustrates a cross section of a ureteral stent 600 composed of three polymers, each with a different hardness. The ureteral stent includes an internal portion 610 composed of a first polymer, an external portion 620 composed of a second polymer and a middle portion 630 composed of a third polymer. The first polymer is the hardest of the three polymers while the second polymer is the softest of the three polymers.

The ureteral stent may optionally be radiopaque. A radiopaque ureteral stent is capable of having its placement confirmed by X-ray or fluoroscopy. The polymers that compose the ureteral stent may be radiopaque, or the stent may include radiopaque markers. For example, a ureteral stent may include radiopaque markers at regular intervals along the length of the ureteral stent, such as every 5 cm.

The ureteral stent may optionally include a coating on the external portion of the ureteral stent. A hydrophilic coating may be used to improve patient comfort or to facilitate insertion. An antibacterial or antimicrobial coating, such as heparin, may be used to reduce infection or encrustation. The ureteral stent may be coated with a single substance, or with a combination of multiple substances.

Figure 7:
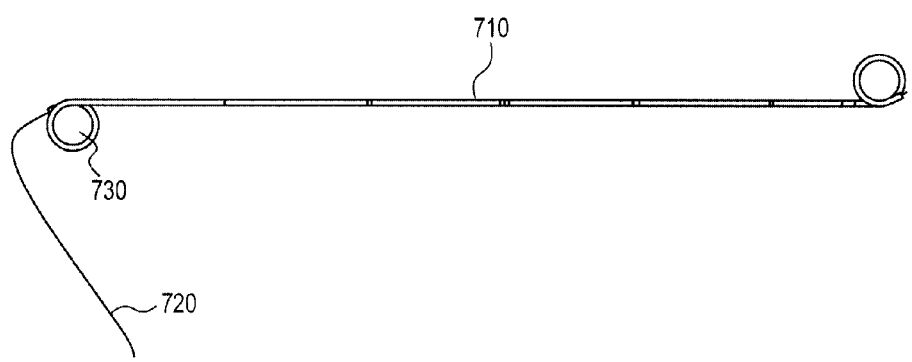
FIG. 7 illustrates a ureteral stent with a string.
Figure 8:
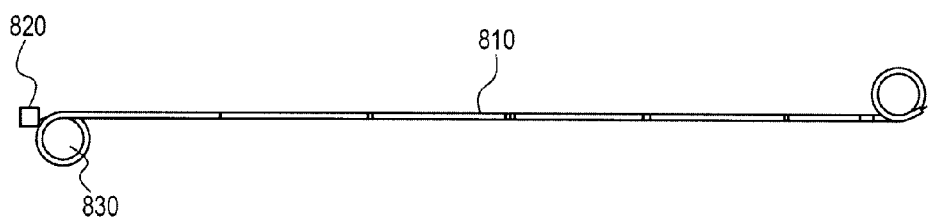
FIG. 8 illustrates a ureteral stent with a magnet.

The ureteral stent may optionally include removal components attached to the bladder end of the ureteral stent. FIG. 7 illustrates a ureteral stent 710 with a string 720. The string extends from the bladder end 730 of the ureteral stent through the urethra and remains outside of the body after the ureteral stent has been placed. A ureteral stent with a string may be removed by pulling on the string. FIG. 8 illustrates a ureteral stent 810 with a small magnet 820. The magnet is attached to the bladder end 830 of the ureteral stent. Preferably, the magnet is a strong magnet, such as a rare earth magnet. A ureteral stent with a magnet may be removed by inserting a catheter with a matching magnet of the opposite polarity through the urethra. After the magnets have coupled, removing the catheter will remove the ureteral stent as well.

The ureteral stent may be provided in a variety of sizes to accommodate the range of ureter lengths that are encountered in adult and pediatric patients. The length of the ureteral stent is sized so that it travels the full length of the ureter and extends into the kidney and the bladder. Suitable lengths for a ureteral stent range from 10-40 cm, preferably 16-28 cm. The outer diameter of the ureteral stent is sized to match the diameter of a typical adult or pediatric ureter. The outer diameter of the ureteral stent may be determined by measuring the terminal portions of two opposite radial projections, or may be determined by measuring the distance from the center of the ureteral stent to the terminal portion of a radial projection and doubling this value. The outer diameter of a ureteral stent may be expressed according to the French catheter scale (abbreviated as Fr, Ga, Fg, FR or F), but may also be measured in units of length such as inches or millimeters. Suitable outer diameters for a ureteral stent range from 3-9 Fr (1-3 mm, or 0.039-0.118 in).

The ureteral stent may be produced by any suitable polymer manufacturing process. The manufacturing process must be capable of creating a monolithic device composed of multiple polymers with different degrees of hardness. The manufacturing process must also be capable of producing a device with the precise dimensions necessary for use in a ureter. Preferably, the ureteral stent is formed by co-extrusion.

Figure 9:
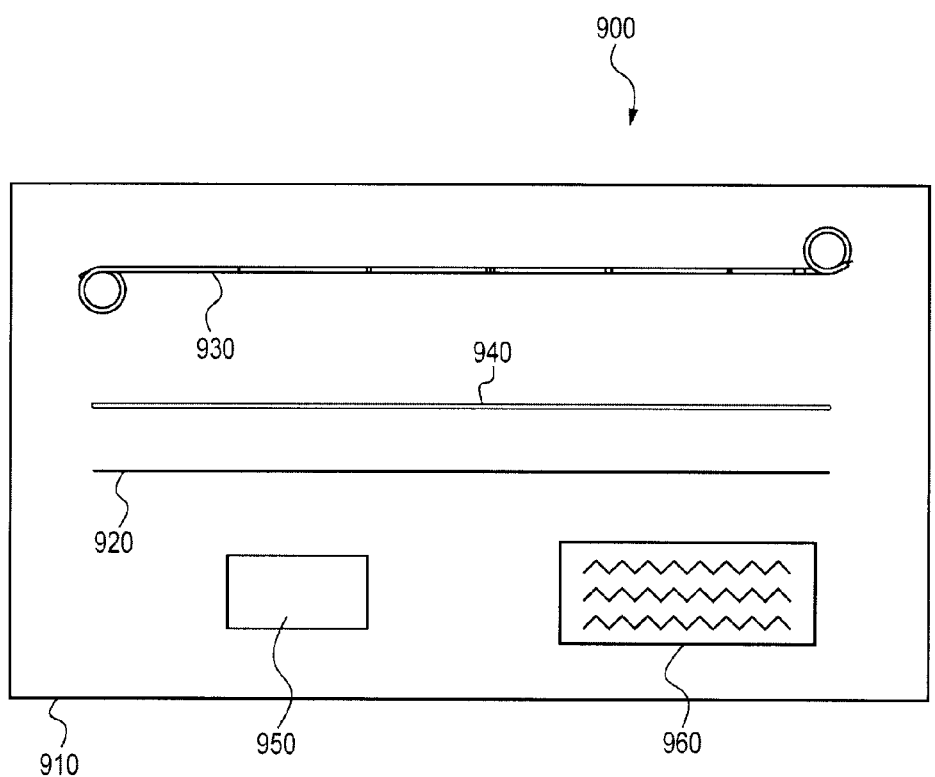
FIG. 9 illustrates a ureteral stent kit.

FIG. 9 illustrates a ureteral stent kit 900. The kit is housed in a container 910. The kit contains a guidewire 920 and a ureteral stent 930. The kit optionally contains a pusher 940. An optional lubricant 950 may be included in the kit. Optional printed instructions 960 describe how to insert the ureteral stent. Preferably, the guidewire, the ureteral stent and any additional components are sterile.

Figure 10:
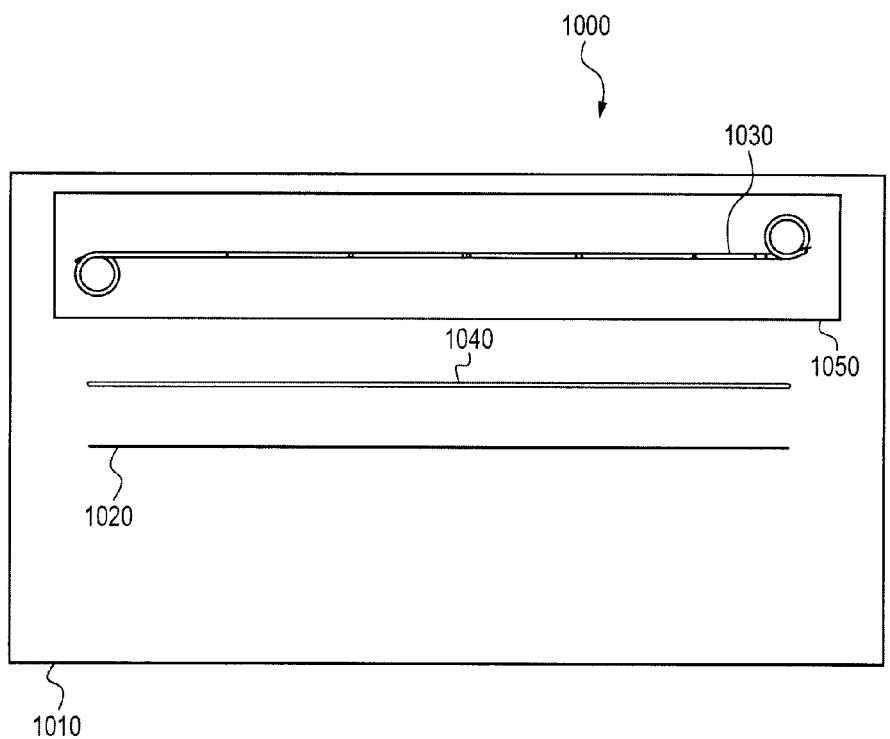
FIG. 10 illustrates a pre-lubricated ureteral stent kit.

The kit may optionally include a lubricant for inserting the ureteral stent. The lubricant may be supplied in a squeezable packet or tube. Alternatively, the ureteral stent may be supplied pre-lubricated. A pre-lubricated ureteral stent may be provided in a sealed package within the kit. FIG. 10 illustrates a pre-lubricated ureteral stent kit 1000. The kit is housed in a container 1010. A pre-lubricated ureteral stent 1030 is stored in a sealed package 1050 within the kit. The kit contains a guidewire 1020 and an optional pusher 1040.

The kit may optionally include instructions for use. The instructions may be provided as printed instructions or in electronic format, such as on a universal serial bus (USB) drive, on a secure digital (SD) card, or hosted over the internet and accessible through a quick response (QR) code.

The kit may optionally include a container for housing the kit ingredients. The container protects the guidewire, ureteral stent and any other components from damage. The container may be formed of a rigid, durable material such as plastic.

Kits may be provided that contain different sized ureteral stents for different intended patients. For example, a kit for use in adult patients may contain a 26 cm ureteral stent with a 9 French outer diameter. Similarly, a kit for use in pediatric patients may contain a 16 cm ureteral stent with a 3 French outer diameter.

The ureteral stent may be inserted into a ureter via the urethra (retrograde stenting) or via an incision through the skin and kidney (antegrade stenting). Retrograde stenting is the preferred insertion method because it is less invasive than antegrade stenting. However, antegrade stenting is appropriate in certain situations, such as when performed in conjunction with a percutaneous nephrolithotomy or when the urethra is not accessible.

In addition to use in humans, the ureteral stent may also be used in animals. An appropriately-sized ureteral stent may be used to maintain the patency of a ureter of an animal in need of treatment. The ureteral stent may be used to treat companion animals, such as dogs and cats, or livestock, such as horses.

EXAMPLES

Example 1

A ureteral stent was formed by co-extruding PEBAX® grade 2533 (Arkema, France) and PEBAX® grade 4033 (Arkema, France). The PEBAX® grade 2533 had a hardness of 25 Shore D and formed the external portion of the ureteral stent. The PEBAX® grade 4033 had a hardness of 40 Shore D and formed the internal portion of the ureteral stent.

Example 2 (Prophetic)

A 50 year old female goes to a urologist complaining of sharp pains in her lower back and difficulty urinating. The urologist performs an X-ray and determines that the patient has a kidney stone in her left kidney. To avoid a blockage of the patient's left ureter, the urologist recommends the insertion of a ureteral stent. The urologist elects retrograde insertion of the ureteral stent. The patient is placed under general anesthesia. A guidewire is inserted through the patient's urethra, bladder, left ureter and into her left kidney with the aid of a cystoscope. A portion of the guidewire remains outside of the patient's body. A radiopaque, dual-hardness ureteral stent with six radial projections, a closed lumen and a small rare earth magnet attached to the bladder end is threaded over the portion of the guidewire extending outside of the patient's body. A pusher is then threaded over the external portion of the guidewire and used to advance the ureteral stent along the guidewire and into the ureter. The placement of the ureteral stent is confirmed by fluoroscopy. The pusher and the guidewire are then removed. After the procedure the patient is able to pass urine through the ureter.

The ureteral stent is non-irritating and the patient does not require medical intervention to address pain. The ureteral stent is removed using a catheter with a matching rare earth magnet after the kidney stone has been broken up and passed.

REFERENCES

1. "Urinary system", available online at en.wikipedia.org/wiki/Urinary_system (Jul. 2, 2015).
2. "Ureter", available online at en.wikipedia.org/wiki/Ureter (Jun. 24, 2015).
3. "Ureteric stent", available online at en.wikipedia.org/wiki/Ureteric_stent (Jul. 1, 2015).
4. "Towers Peripheral Ureteral Stent Set", Cook Medical, available online at www.cookmedical.com/products/uro_towerswebds/ (2015).
5. Singh, I., "Indwelling JJ ureteral stents—a current perspective and review of literature", Indian Journal of Surgery, Vol. 65, No. 5, pp. 405-412 (September-October 2003), available online at www.bioline.org.br/request?is03080.
6. "PEBAX® Polyether Block Amides", Arkema, available online at www.PEBAX.com/export/sites/PEBAX/content/medias/downloads/literature/PEBAX-product-range-brochure.pdf (Downloaded on Jul. 17, 2015).

What is claimed is:

1. A ureteral stent, consisting of:
an internal portion, comprising a first polymer, and
an external portion surrounding the internal portion and forming 2-10 radial projections that extend along the length of the ureteral stent, comprising a second polymer,
wherein the second polymer has a Shore D hardness of 20-40 Shore D, and
the first polymer has a Shore D hardness that is at least 10 units greater than the Shore D hardness of the second polymer.

2. The ureteral stent of claim 1, wherein the internal portion defines a lumen.

3. The ureteral stent of claim 1, wherein the internal portion does not define a lumen.

4. The ureteral stent of claim 1, wherein the ureteral stent is not coiled.

5. The ureteral stent of claim 1, wherein the first polymer has a hardness of 35-70 Shore D.

6. The ureteral stent of claim 1, wherein the first polymer and the second polymer consist of thermoplastic elastomers.

7. The ureteral stent of claim 1, wherein the first polymer and the second polymer consist of polyether block amides (PEBAs).

8. The ureteral stent of claim 1, wherein the radial projections are substantially normal to the external portion.

9. The ureteral stent of claim 1, wherein the radial projections are curved.

10. The ureteral stent of claim 1, wherein the radial projections have the shape of one or more lobes extending from the terminal portion of the radial projections.

11. The ureteral stent of claim 1, wherein the ureteral stent is sterile.

12. A coated ureteral stent, comprising:
the ureteral stent of claim 1, and
a coating on the external portion,
wherein the coating is selected from the group consisting of hydrophilic coatings, antibacterial coatings, antimicrobial coatings, and combinations thereof.

13. The ureteral stent of claim 1, wherein the external portion forms 6 radial projections,
the first polymer has a hardness of 40 Shore D,
the second polymer has a hardness of 25 Shore D,
the first polymer and the second polymer consist of polyether block amides,
the radial projections are substantially normal to the external portion, and
the ureteral stent is sterile.

14. A kit, comprising:
a guidewire, and
the ureteral stent of claim 1,
wherein the guidewire and the ureteral stent are sterile.

15. The kit of claim 14, further comprising a pusher.

16. The kit of claim 14, further comprising a pusher,
a container,
a lubricant, and
printed instructions,
wherein the guidewire and the ureteral stent are housed in the container, and
the guidewire is pre-threaded through the ureteral stent.

17. A ureteral stent, consisting of:
an internal portion, comprising a first polymer,
an external portion surrounding the internal portion and forming 2-10 radial projections that extend along the length of the ureteral stent, comprising a second polymer, and
a middle portion comprising a third polymer,
wherein the second polymer has a Shore D hardness of 20-40 Shore D, and
the first polymer has a Shore D hardness that is at least 10 units greater than the Shore D hardness of the second polymer.

18. A coated ureteral stent, comprising:
the ureteral stent of claim 17, and
a coating on the external portion,
wherein the coating is selected from the group consisting of hydrophilic coatings, antibacterial coatings, antimicrobial coatings, and combinations thereof.

* * * * *